US010722258B2

(12) United States Patent
Batchelor et al.

(10) Patent No.: US 10,722,258 B2
(45) Date of Patent: Jul. 28, 2020

(54) SURGICAL DEVICE HAVING ATRAUMATIC TISSUE CONTROL

(71) Applicant: GYRUS ACMI, INC., Southborough, MA (US)

(72) Inventors: Kester J. Batchelor, Mound, MN (US); Huisun Wang, Maple Grove, MN (US); Theodore C. Blus, Shoreview, MN (US)

(73) Assignee: Gyrus Acmi, Inc., Southborough, MA (US)

( * ) Notice: Subject to any disclaimer, the term of this patent is extended or adjusted under 35 U.S.C. 154(b) by 211 days.

(21) Appl. No.: 15/850,090

(22) Filed: Dec. 21, 2017

(65) Prior Publication Data

US 2019/0192178 A1 Jun. 27, 2019

(51) Int. Cl.
*A61B 17/29* (2006.01)
*A61B 18/14* (2006.01)
(Continued)

(52) U.S. Cl.
CPC .......... *A61B 17/29* (2013.01); *A61B 18/1445* (2013.01); *A61B 17/2909* (2013.01); (Continued)

(58) Field of Classification Search
CPC . A61B 17/2812; A61B 17/29; A61B 17/2909; A61B 17/30; A61B 17/3201; A61B 18/1445; A61B 2017/00561; A61B 2017/2926; A61B 2017/306; A61B 2018/1455; A61B 2217/005; A61B 2217/007; A61B 2218/007
See application file for complete search history.

(56) References Cited

U.S. PATENT DOCUMENTS 3,495,593 A   2/1970 Snyder
3,807,406 A   4/1974 Rafferty et al.
(Continued)

FOREIGN PATENT DOCUMENTS

| EP | 2174612 A1 | 4/2010 |
|----|------------|--------|
| WO | 2001/045574 A1 | 6/2001 |
| WO | 2012/022122 A1 | 2/2012 |

*Primary Examiner* — Katherine M Shi
(74) *Attorney, Agent, or Firm* — Schwegman Lundberg & Woessner, P.A.

(57) ABSTRACT

A surgical device comprising: (a) a first jaw having a face; (b) a second jaw having a face that is substantially adjacent the face of the first jaw when the first jaw and the second jaw are in a closed position; (c) a pivot connecting the first jaw and the second jaw together so that the first jaw and second jaw are movable between an open position and the closed position; (d) one or more fluid passageways extending between the first jaw, the second jaw, or both and a region outside of the surgical device so that fluid passes through the first jaw, the second jaw, or both; and (e) a valve connected to the first jaw, the second jaw, or both, the one or more fluid passageways extending through the valve so that when the first jaw and the second jaw are in the open position the valve is open and fluid can extend through the one or more fluid passageways and when the first jaw and the second jaw are in the closed position the valve is closed and fluid is prevented from flowing through the one or more fluid passageways.

19 Claims, 6 Drawing Sheets

(51) Int. Cl.
*A61B 17/00* (2006.01)
*A61B 17/30* (2006.01)

(52) U.S. Cl.
CPC ............... *A61B 2017/00561* (2013.01); *A61B 2017/2925* (2013.01); *A61B 2017/2926* (2013.01); *A61B 2017/2936* (2013.01); *A61B 2017/306* (2013.01); *A61B 2018/1455* (2013.01); *A61B 2218/007* (2013.01)

(56) References Cited

U.S. PATENT DOCUMENTS

| | | | |
|---|---|---|---|
| 3,916,909 A | | 11/1975 | Kletschka et al. |
| 4,049,002 A | * | 9/1977 | Kletschka .......... A61B 17/2812 604/35 |
| 4,096,864 A | * | 6/1978 | Kletschka .............. A61B 17/30 604/35 |
| 4,977,900 A | | 12/1990 | Fehling et al. |
| 5,167,618 A | | 12/1992 | Kershner |
| 5,192,292 A | * | 3/1993 | Cezana ............ A61B 17/32002 604/22 |
| 5,217,460 A | | 6/1993 | Knoepfler |
| 5,250,075 A | | 10/1993 | Badie |
| 5,445,638 A | | 8/1995 | Rydell et al. |
| 5,498,246 A | | 3/1996 | Deutchman et al. |
| 5,603,712 A | | 2/1997 | Koranda et al. |
| 5,647,871 A | | 7/1997 | Levine et al. |
| 5,745,739 A | | 4/1998 | Wang et al. |
| 6,113,596 A | | 9/2000 | Hooven et al. |
| 6,190,386 B1 | | 2/2001 | Rydell |
| 6,290,705 B1 | | 9/2001 | Chan et al. |
| 6,485,436 B1 | | 11/2002 | Truckai et al. |
| 6,632,182 B1 | | 10/2003 | Treat |
| 6,679,882 B1 | | 1/2004 | Kornerup |
| 6,863,669 B2 | | 3/2005 | Spitzer |
| 6,926,717 B1 | | 8/2005 | Garito et al. |
| 7,118,587 B2 | | 10/2006 | Dycus et al. |
| 7,150,747 B1 | | 12/2006 | McDonald et al. |
| 7,604,635 B2 | | 10/2009 | McClurken et al. |
| 8,353,907 B2 | | 1/2013 | Winkler et al. |
| 8,382,654 B2 | | 2/2013 | Taylor |
| 8,734,443 B2 | | 5/2014 | Hixson et al. |
| 8,740,898 B2 | | 6/2014 | Chojin et al. |
| 8,961,430 B2 | | 2/2015 | Coonahan et al. |
| 9,241,692 B2 | | 1/2016 | Gunday et al. |
| 2003/0114850 A1 | | 6/2003 | McClurken et al. |
| 2004/0068291 A1 | * | 4/2004 | Suzuki ............... A61B 10/0096 606/205 |
| 2005/0033278 A1 | * | 2/2005 | McClurken ............ A61B 18/14 606/41 |
| 2005/0245841 A1 | | 11/2005 | Turturro et al. |
| 2009/0270789 A1 | | 10/2009 | Maxymiv et al. |
| 2011/0306968 A1 | | 12/2011 | Beckman et al. |
| 2015/0141980 A1 | | 5/2015 | Jadhav et al. |
| 2016/0091098 A1 | * | 3/2016 | Mosher ................. F16K 5/0478 251/309 |
| 2016/0157703 A1 | | 6/2016 | Brooks et al. |
| 2016/0184005 A1 | | 6/2016 | Singh |
| 2016/0278844 A1 | | 9/2016 | Zamarripa et al. |

\* cited by examiner

SURGICAL DEVICE HAVING ATRAUMATIC TISSUE CONTROL

FIELD

The present teachings relate to forceps with a first jaw and a second jaw that are movable relative to each other and one or both of the jaws include a fluid opening that assists in retaining tissue between the first jaw and the second jaw as the jaws are closed to grip the tissue.

BACKGROUND

Generally, forceps may be utilized for laparoscopic surgery. The forceps may be used to control delicate movements inside a patient. These forceps may be used to grip an anatomical feature. The forceps may include a gripping assembly or a cutting assembly. The forceps may include electrical energy for use in the gripping assembly. The forceps have a pair of opposed resilient jaws that are closed against each other by pulling the jaws into a distal end of a shaft that captures a portion of the jaws that is wider than the distal end opening of the shaft so that the jaws are moved together. Similarly, the tube may be pushed over the jaws so that the jaws are moved together to create a gripping force. In both of these the tubes capture a portion of the jaws and acts as a cam that forces the jaws together to create the gripping force. Other forceps may include a pivot and movement of ends of the forceps opposite the jaws may cause the jaws to rotate closed about the pivot. Examples of some forceps may be found in U.S. Pat. Nos. 5,445,638; 6,190,386; 6,113,596; 6,679,882, 7,118,587, and 8,734,443 all of which are incorporated by reference herein in their entirety for all purposes. During gripping of the anatomical feature such as tissue the anatomical feature may slip out from between the jaws and re-gripping may be needed in order to grip the anatomical feature between the jaws. Furthermore, repeated gripping of the anatomical feature of over-gripping (e.g., a high application of force) could potentially damage or injure the anatomical feature requiring additional healing or treatment.

It would be attractive for the forceps to include a device that includes atraumatic tissue control that assists in maintaining the tissue between the jaws. What is needed is forceps that includes one or more fluid openings that assist in retaining an anatomical feature between the jaws so that the anatomical feature can be gripped without the need for re-gripping or over-gripping. What is needed is forceps that are connected to a suction source and the suction source creates a vacuum at the jaws and the vacuum assists in holding an anatomical feature against one or both of the jaws so that the anatomical feature is retained in place while a clamping force is applied. It would be attractive to have one or more jaws that include one or more conduction plates assist in applying power to the anatomical features. What is needed is one or more jaws that include teeth that assist in retaining the anatomical feature between the jaws.

SUMMARY

The disclosure meets one or more of the needs by providing: surgical device comprising: (a) a first jaw having a face; (b) a second jaw having a face that is substantially adjacent the face of the first jaw when the first jaw and the second jaw are in a closed position; (c) a pivot connecting the first jaw and the second jaw together so that the first jaw and second jaw are movable between an open position and the closed position; (d) one or more fluid passageways extending between the first jaw, the second jaw, or both and a region outside of the surgical device so that fluid passes through the first jaw, the second jaw, or both; and (e) a valve connected to the first jaw, the second jaw, or both, the one or more fluid passageways extending through the valve so that when the first jaw and the second jaw are in the open position the valve is open and fluid can extend through the one or more fluid passageways and when the first jaw and the second jaw are in the closed position the valve is closed and fluid is prevented from flowing through the one or more fluid passageways.

The teachings herein provide forceps that include a device having atraumatic tissue control that assists in maintaining the tissue between the jaws. The teachings herein provide forceps that include one or more fluid openings that assist in retaining an anatomical feature between the jaws so that the anatomical feature can be gripped without the need for re-gripping or over-gripping. The teachings herein provide forceps that are connected to a suction source and the suction source creates a vacuum at the jaws and the vacuum assists in holding an anatomical feature against one or both of the jaws so that the anatomical feature is retained in place while a clamping force is applied. The teachings herein provide one or more jaws that include one or more conduction plates assist in applying power to the anatomical features. The teachings herein provide one or more jaws that include teeth that assist in retaining the anatomical feature between the jaws.

DETAILED DESCRIPTION

Figure 1:
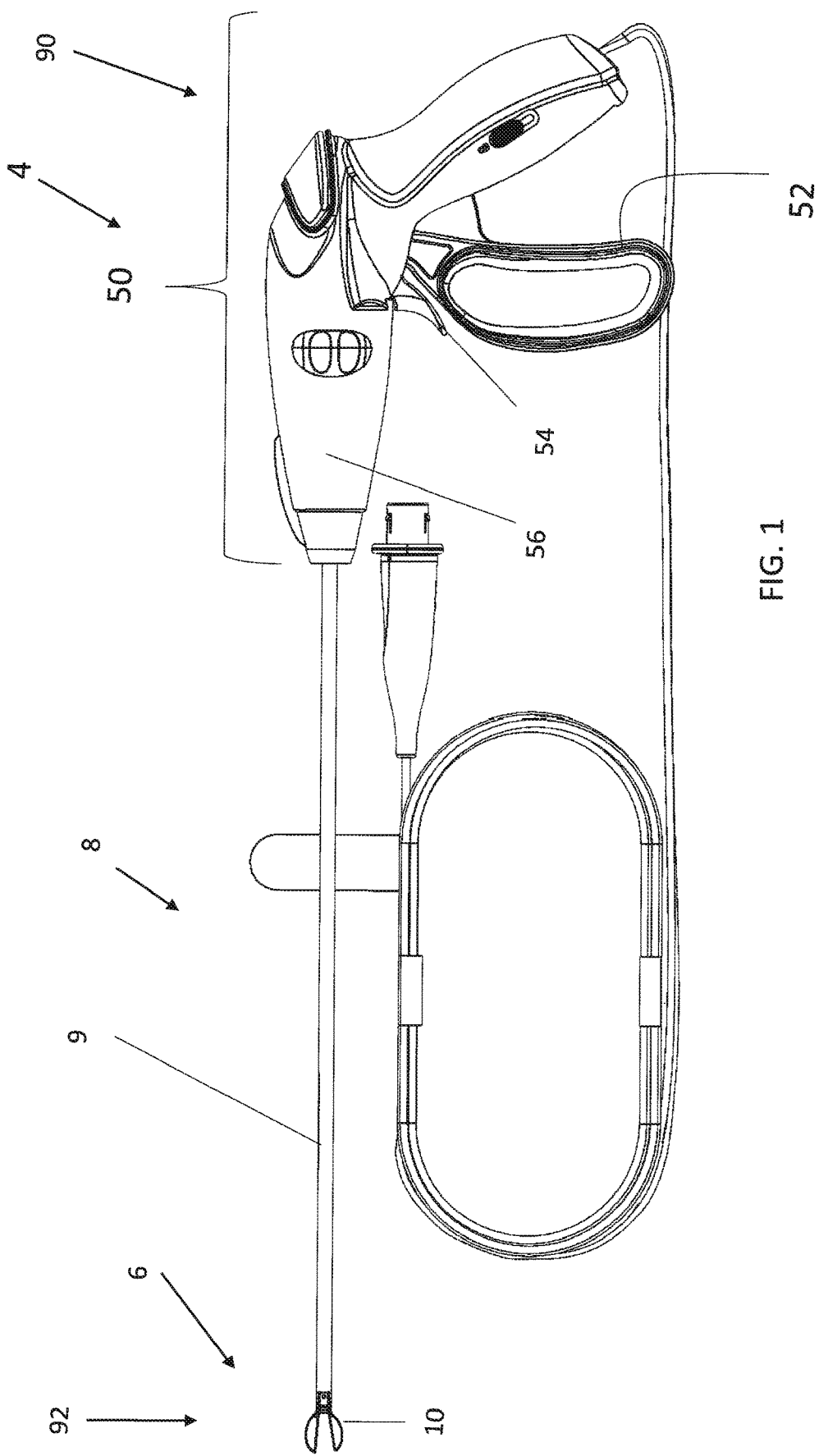
FIG. 1 is a side view of a surgical device.

The explanations and illustrations presented herein are intended to acquaint others skilled in the art with the teachings, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

The present teachings relate to a surgical device. The surgical device may be a non-electrical device (i.e., may only provide mechanical functions). Preferably, the surgical device is an electrosurgical device. The electrosurgical device may provide one or more therapy currents. Preferably, the electrosurgical device provides two or more therapy currents (e.g., monopolar power and bipolar power). A therapy current may pass between the jaws (e.g., bipolar power). A therapy current may pass from a jaw to a blade or vice versa. A therapy current (e.g., monopolar power) may pass from a blade to a remote electrode (e.g., ground pad). The electrosurgical device may apply power before, after, or simultaneously with a mechanical technique (e.g., gripping or cutting). The electrosurgical device may include a distal end and a proximal end. The distal end may include a portion of a forceps device (e.g., jaws, blade, or both). The distal end may be a portion of the surgical device that is farthest from a user. The proximal end may be a portion a user grips (e.g., hand piece or housing) or a portion closest to a user.

The hand piece may function to form an enclosing structure for the forceps, a gripping portion for the user, a main portion for manipulating the forceps, or a combination thereof. The hand piece may be any device that houses all or a portion of the working assemblies and parts of the forceps. The hand piece may be comprised of one or more housing structures. Preferably, the hand piece is two or more housing structures. The hand piece may be any structure that is gripped by a user. The hand piece may be any structure that combines one or more of the components discussed herein so that the surgical device is formed. The hand piece may assist in performing laparoscopic surgery. The hand piece may be ergonomically shaped. The ergonomic shape of the hand piece may be any shape so that the forceps may be used ambidextrously. The ergonomic shape of the hand piece may be any shape such that all the controls can be accessed by a single hand gripping the hand piece. The hand piece may be comprised of housing structures. The housing structures may be one or more devices that form the hand piece. The housing structures may be any devices that may affix certain pieces into position. The housing structures may form a cavity to house working assemblies of the forceps. The housing structures may be one or more housing structures and preferably two or more housing structures. The housing structures may be any device that includes a recess for receiving one or more components of the forceps. The housing structures may house all or a portion of one or more operable mechanisms, one or more valves, or both. The housing structure may house all or a portion of an operable mechanism that causes the jaws to move, the blade to move, the valve to open, the valve to close, or a combination thereof. The housing structure may be made of one or more housings.

The one or more housings may function to form a hand piece, enclose a portion of an operable mechanism, form a portion of a four bar mechanism, enclose a portion of a stylet, enclose one or more tubes, or a combination thereof. The one or more housings may be a left half and a right half. The housing may be multiple pieces that are connected together. The housing may be made of plastic. The housing may be a combination of plastic and metal. The housing may include a grip. The housing may include one or more links (e.g., a cut lever/cut trigger or a clamp lever/clamp trigger) extending therefrom. The housing may be free of links. The housing may be connected to a first jaw, a second jaw, or both jaws of forceps and a direct force may be applied to the housings in order to move the forceps towards or apart from each other. For example, upon a force upon the housing the jaws may move towards each other. In another example, upon a force upon the housing the jaws may move apart. The housing may house all or a portion of the four bar mechanism. The housing be a proximal end (e.g., end closest to a user) and the jaws or blade may be the distal end (e.g., end farthest from a user). However, the housing may extend from a proximal end to substantially the distal end. The jaws, blade, first link, second link, third link, fourth link, four bar mechanism, tube, or a combination thereof may be moved between a first position (release position) and a second position (retract position) by one or more operable mechanism or direct contact by a user.

The one or more operable mechanism may function to move one or more jaws, both jaws, a blade, one or more valves, or a combination thereof. The one or more operable mechanism may include a four bar mechanism, a five bar mechanism, or even a six bar mechanism. The operable mechanism may include one or more rods (e.g., a blade support rod, a jaw support rod, or both). The one or more operable mechanisms may be or include one or more levers, links, triggers, or a combination thereof. The one or more operable mechanism may include a cut lever or cut trigger (e.g., that moves a blade), a clamp lever or cut trigger (e.g., that moves the jaws between a release position and a retract position), or both. The one or more levers may be an input that a user actuates to activate the operable mechanism. The one or more levers may be part of the operable mechanism. One lever or trigger may be part of the operable mechanism and one lever or trigger may be separate from the operable mechanism. The one or more operable mechanisms may be any device that may be manipulated or moved by applying pressure or a force to a portion of the one or more operable mechanisms with a hand, finger, foot, or a combination thereof to produce an output movement on an output element or apply an output force on an output element. The one or more operable mechanisms may be any device that may connect other moveable components, for example the tubular member, a cutting assembly, a blade assembly, a functional assembly, a jaw, a jaw support rod, a valve, or a combination thereof together. The one or more operable mechanisms may be actuated ambidextrously. The one or more operable mechanisms may be a single operable mechanism that may be linked to two different functions and may be moved to generate each function simultaneously. For example, the operable mechanism may close two jaws together and move a blade between the two jaws. In another example, the operable mechanism may close two jaws together and close a valve so that the fluid is prevented from extending through a fluid line that extends from one or both of the jaws and a location external of the hand piece, the forceps, the surgical device, or a combination thereof. The operable mechanism may function to convert rotational movement into longitudinal movement. An operable mechanism may function to axially move one or more jaws, one or tubes (e.g., hollow tubes or solid tubes), one or more blades, or a combination thereof. The operable mechanism may include one or more tubes, support rods, or both. Each axially or rotationally moving member may be connected to an operable mechanism. Preferably, the operable mechanism causes the jaws to rotate about a pivot so that the jaws move between an open position and a closed position and the valve moves between an open position and a closed position. The operably mechanism may be actuated by one or more triggers (e.g., a cut trigger, a clamp trigger, or both).

The one or more triggers function to be an input to an operable mechanism. The one or more triggers as discussed herein may be a lever, handle, link, or a combination thereof. The one or more triggers may be a cut trigger, a clamp trigger, or both that when actuated input movement into the operable mechanism so that the operable mechanism provides an output. If the triggers are a lever, the lever is a rigid member that turns on a pivot. The cut lever or cut trigger, the clamp lever or clamp trigger, or both may be a first link of an operable mechanism or a respective four bar mechanism. The cut lever, the clamp lever, or both may be a first link. The cut lever, the clamp lever, or both may function to move one or more jaws, one or more blades, a jaw support rod, a blade support rod, a second link, one or more valves, or a combination thereof. The cut lever, the clamp lever, or both may extend between a release position (e.g., a start position) and a retract position (e.g., a full pull position where the jaws are closed, a valve is closed, the blade is extended, or a combination thereof). The cut lever, the clamp lever, or both as they extend from a start position to a full pull-position may close jaws, close a valve, extend a blade, or a combination thereof. For example, as the clamp trigger is moved, the clamp trigger may begin to close the jaws and as the jaws close the valve may simultaneously be closed such that an amount of fluid passing through the jaws is decreased until the jaws are closed.

The return mechanism may assist in actuating the triggers (e.g., cut trigger, the clamp trigger, or both). The return mechanism may return the one or more triggers to a neutral position and/or a starting position after actuation. The return mechanism may be any device that biases one or more of the links to a resting position so that when one or more of the triggers are actuated and released from actuation the tubular member, stylet, jaws, blade, valves, triggers, or a combination thereof return back to a resting position. The return mechanism may be located on a distal side or a proximal side of one or more of the triggers. The return mechanism may be located on a distal side or a proximal side of a blade, jaws, valve, pivot, tube, or a combination thereof. Preferably, a return mechanism is located on a proximal side of one or more components of a stylet (e.g., a jaw support rod, a blade support rod, tube, or a combination thereof. The return mechanism may be and/or include a biasing member (e.g., a spring structure, an elastic member, a compressible member, a stretchable member, any structure that can be compressed and released, any structure that can store and release energy, or a combination thereof). The return mechanism may be a return spring or a compression spring. The return mechanism may be connected to a proximal end of a stylet, a tubular member, a link of a four bar mechanism (e.g., a first link, a second link, a third link, a fourth link), an operable mechanism, or a combination thereof. The return mechanism may assist in moving a first link from a first position to a second position so that the jaws (e.g., forceps) of the electrosurgical device are moved between a closed position and an open position, a valve is moved between a closed position and an open position, or both. Preferably, the return mechanism assists in moving one or more jaws of forceps.

The present teachings provide a forceps device. The forceps may function to grip an object. Preferably, the forceps may be used during surgery to grip a feature of interest including: a part of a body, an anatomical feature, tissue, veins, arteries, or a combination thereof. The forceps may move between a first position (e.g., release position) and a second position (e.g., retract position). The forceps may be fully closed in a full-pull position or partially closed in a partial pull position. The forceps may function to be used in surgery, for example laparoscopic surgery. The forceps may be used with or without power. Current may be passed through the forceps (e.g., a conduction plate) so that the forceps are used for electro-surgery. For example, a therapy current may be passed from one jaw to a second jaw when tissue is located within the jaw and the therapy current may coagulate blood, cauterize, cut, or a combination thereof. In another example, a therapy current may be passed from one or more of the jaws to a remote electrode (e.g., a return pad). The forceps may generally include one or more working assemblies and sufficient controls to work the one or more assemblies. The forceps may be comprised of parts needed to perform the recited functions and may include generally, a stylet (e.g., a tubular member, a hollow tube, or an assembly of tubes), a hand piece, one or more operable mechanisms used to actuate the stylet, one or more valves, or a combination thereof. The hand piece may be an assembly of parts or housing structures capable of forming a hand piece structure with a cavity. The forceps may be actuated by one or more operable mechanisms. The forceps may be actuated by direct pressure being applied to one or both of the jaws so that the jaws are moved towards or away from each other (e.g., laterally moved). The forceps may create a sufficient gripping force so that one or more features of interest of a patient's body may be manipulated by the gripping assembly, secured by the gripping assembly, or a combination thereof. The forceps may include atraumatic tissue control that assists the forceps in gripping a feature of interest. The atraumatic tissue control may create vacuum at one or more faces of the jaws of the forceps that assist in holding the feature of interest within the forceps as the forceps are closed. The atraumatic tissue control may reduce an amount of assistance as a force applied by the forceps increases. The amount of assistance applied by the atraumatic tissue control may be inversely proportional to the amount of force applied by the forceps to a feature of interest. The forceps may be composed of parts that may extend through a tubular member. The forceps may be part of a stylet. The forceps may be free of any members that extend through a tubular member. For example, the forceps may be configured as tweezers that are used in open surgery and the user may directly grasp portions of the forceps. The forceps may be an assembly of parts rotatable about an axis (e.g., a rotational axis of the forceps, the longitudinal axis of the tubular member, a longitudinal axis of the forceps, or a combination thereof). The forceps may grip and release while being simultaneously rotated. The forceps may be actuated by the actuation mechanism in communication with the forceps or a user directly contacting the forceps. The forceps may be actuated by retracting the two opposing jaws into the stylet (e.g., one or more tubular members) forcing the two opposing jaws closed. The forceps may be actuated by extending the one or more tubular members away from the hand piece (e.g., distally) so that the one or more tubular members move the two opposing jaws towards one another into a retracted position, creating a gripping force, or both. The forceps may generally have two or more opposing jaws, and one or more jaw shafts or legs, one or more valves, or a combination of both. Preferably, the forceps may have two jaw shafts or legs that each include an arcuate section and an opposing jaw attached to each of the jaw shafts or legs so that the forceps may be moved between a release position and a retract position.

The release position may be where no external forces are acting on a clamp trigger, cut trigger, first jaw, second jaw, or a combination thereof. The release position may be a neutral position. The release position may be where the jaws are open. The release position may be where the blade is proximally retracted. The release position may be where the bias device biases the electrosurgical device to a resting position. The release position may be where a valve is open so that fluid can freely move through the fluid line, the valve, or both. Upon an application of force or torque the forceps, valve, jaws, blade, or a combination thereof may move from a release position to a retract position.

The retract position may be where a feature of interest is gripped, cut, held, or a combination thereof. The retract position may have one or more jaws closed. The retract position may be where a valve is closed and fluid is prevented from passing through one or more fluid lines. The retract position may have a trigger fully depressed (i.e., retracted). The retract position may have the one or more housings pressed together. The retract position may have a blade extended from a distal end of a stylet, tube, or both. The retract position may be where the stylet is moved distally, the jaw shafts are moved proximally, the blade shafts are moved distally; the jaws rotate about a pivot, or a combination thereof.

The stylet as discussed herein may include a tubular member or may be the tubular member (i.e., tube). The stylet may have a hollow cross-section, a solid cross-section, or both. The stylet may include one or more tubes and one or more shafts may extend through the tubes. For example, an inner tube may be solid and an outer tube may be hollow. The stylet may include a tubular member and an inner tube. The stylet may include a tube that extends around all or a portion of an inner tube. The stylet may be a hollow tube with one or more shafts extending through the hollow tube. The stylet may function to extend into a patient during a surgical procedure so that a user (i.e., surgeon) can perform one or more surgical procedures. The stylet may be flexible so that the stylet may be moved within a patient. Preferably, the stylet may be substantially rigid so that the stylet may be moved to a desired location. The stylet includes a distal end and a proximal end. The distal end may be an end of the stylet that is located farthest from the hand piece (e.g., the end of the stylet that is inserted into a patient). The proximal end of the stylet may be the end of the tube located proximate to the user, in the hand piece, or both. For example, the proximal end may extend into the hand piece so that manipulation of the one or more operable mechanisms manipulates the tube. The stylet and its components may be made of any biocompatible material, for example, stainless steel, plastic, a synthetic material, a natural material, or a combination thereof. The stylet may comprise a tube sub-assembly. The tube sub-assembly may include one or more tubes, one or more inner tubes, one or more outer tubes, one or more gripping assemblies, one or more cutting assemblies, one or more rotation mechanisms, one or more operable mechanisms, one or more camming shafts, one or more guides, one or more spacing members, one or more valves, one or more jaw shafts, one or more blade shafts, or a combination thereof.

The one or more outer tubes may function to close the jaws, bias the jaws, or both. The one or more outer tubes may function to house one or more jaws, one or more blades, or both. The one or more tubes may house a valve. The one or more tubes may function to bias the actuation mechanisms that bias the jaws. The one or more tubes may function to protect the inner tube. The one or more jaws may move relative to the inner tube. The one or more jaws may axially move towards the distal end and the proximal end during movement. Preferably, the one or more outer tubes may be hollow. The one or more jaws may overrun the inner tube, the jaws, the arcuate sections, or a combination thereof to bias the jaws towards each other. The one or more inner tubes may function to create a point of contact for one or more jaws. The one or more inner tubes may function to connect to a camming shaft. The one or more inner tubes may function to extend through all or a portion of the stylet. The one or more inner tubes may form a connection point, include a connection feature (e.g., a pin, bolt, screw, rivet, or a combination thereof) for one or more jaws. The one or more inner tubes may connect to a pivot joint of one or more jaws so that the one or more jaws rotate about an axis. The one or more inner tubes may assist in opening and closing the jaws, valves, or both. The one or more inner tubes may be located distal of one or more tubes. The one or more inner tubes may be part of a tubular member or a stylet. The one or more inner tubes may be movable relative to an outer tube. The one or more inner tubes may be axially movable, rotationally movable, or both relative to an outer tube, a camming shaft, or both. The one or more inner tubes may be static and an outer tube may be movable relative to the inner tube. The one or more inner tubes may be substantially the same length as an outer tube. The one or more inner tubes may be shorter than an outer tube. The one or more inner tubes may be in communication with a camming shaft. The one or more inner tubes may be hollow. The one or more inner tubes may be solid. The one or more forceps may be free of any tubes or tubular members. The one or more inner tubes may be located between a tubular member and a tube.

The one or more tubular members may include and/or be one or more tubes and the one or more tubes (e.g., an inner tube, an outer tube, an intermediate tube between an inner tube and an outer tube) may function to house one or more working components (e.g., a gripping assembly, a cutting assembly, a valve, jaw shafts, blade shafts, or a combination thereof). The one or more tubular members may function to house all or a portion of one or more functional members (e.g., inner tube, blade, jaws).

The two or more opposing jaws may function to create a gripping force. The two or more opposing jaws may move towards each other to create a gripping force, to grip a feature of interest, or both. The two or more opposing jaws may be any device that may be used to grip items of interest in surgery, for example laparoscopic surgery. The two or more opposing jaws may function to be used to grip or clamp an item of interest for cutting or applying a bipolar energy source. The two or more opposing jaws may be any shape and size so that the jaws perform a gripping function, create a gripping force, or both. Preferably, the two or more opposing jaws may be one jaw structure with another mirror image opposing jaw structure (i.e., identical) that when forced together may create a gripping function. The two opposing jaws may be any two or more structures that may be movable relative to each other for perform a gripping function. The two opposing jaws may be any structures that may allow one jaw to be static and one jaw to be movable or any combination thereof. The two opposing jaws may be one solid piece. Each of the two opposing jaws may be substantially sold and may include one or more fluid openings, one or more conduction plates, one or more teeth, mesh, channels, or a combination thereof. The two opposing jaws may be formed of two wires that are shaped to have a generally "U" shaped end. The two opposing jaws may be made of any material so that the two opposing jaws may be used to create a gripping force. The two opposing jaws may be made of a flexible material, resilient material, rigid stainless steel, a plastically deformable material, an elastically deformable material, or a combination thereof. The two opposing jaws may be made of a material that conducts electricity. The two opposing jaws may include a channel (e.g., a blade track) to allow for a cutting instrument to be inserted while retaining functionality of the two or more opposing jaws.

The channel may be any shape and size so that a blade, functional element, a surgical instrument, or a combination thereof may be extended into the channel in the jaws, into the channel between the jaws, or both. The blade, a surgical instrument, functional element, or a combination thereof may be extended into the channel formed in (or between) the two opposing jaws while the two opposing jaws are closed, open, or in a position therebetween. The channel may be formed in the opposing jaws, the jaws may be made of a wire material that may be formed to include the gap, material may be removed to form the gap, or a combination thereof. The channel (e.g., blade track) may extend along the longitudinal axis of the tubular member, blade, or both so that the blade axially extends into the channel during use. The material the jaws are made of may be formed to include a channel. The channel may be an absence of material in one or both of the jaws. The channel may extend through substantially the center of each jaw so that the jaws are generally "U" or "C" shaped. The jaws may include a protective cover.

The protective cover may function to prevent current leakage, prevent application of power to an undesired location, insulate the wires, create a contact location at a predetermined location, or a combination thereof. The protective cover may protect an outside of the jaws. The protective cover may prevent stray current. The protective cover may assist in directing current to a desired location. The protective cover may be made of an insulating material. The protective cover may be made and/or include rubber, plastic, a polymer, plastic, an insulative material, or a combination thereof. The protective cover may be a portion of the housing that extends over each of the jaws. The protective cover may be contacted by a user so that the jaws are closed. The protective cover may cover only a portion of the jaws so that the jaws may apply power. The protective cover may be located opposite a conduction plate or a portion of the jaws where power is applied.

The two opposing jaws may be used to apply electricity to a feature of interest that may be gripped by the two opposing jaws. The two opposing jaws may be a first jaw and a second jaw. The first jaw may be movable relative to the second jaw, or vice versa. The first jaw and second jaw may be longitudinally movable relative to each other. Preferably, the first jaw and second jaw longitudinally move in unison. The first jaw and second jaw may be longitudinally static. The first jaw and second jaw may move about a pivot towards and away from each other. The first jaw, the second jaw, or both may laterally move relative to each other (i.e., linearly directly towards and away from each other). The gripping portion of the two opposing jaws may have a surface texture to grip a feature of interest (e.g., teeth or mesh). For instance the surface texture may be smooth, flat, contoured, serrated, textured, include ridges, mouse teeth, or a combination thereof. Preferably, the gripping portion of the two opposing jaws may have a serrated edge to allow for more secure gripping. The two opposing jaws may have an edge with a surface that may function similar to a serrated edge to allow for secure gripping. The two opposing jaws may be moved between a release position and a retract position by retraction of one of the one or more jaw shafts, movement of the one or more tubular members towards the distal end, or both along an axis of the one or more tubular members; an application of force by a user; or a combination thereof. The two opposing jaws may include a jaw bias mechanism, be part of an operable mechanism, or both. The two opposing jaws may have laterally extending arcuate sections at the proximal end (e.g., heel of the jaw) of the jaws that protrude out from the distal end of the tubular member, while one or more jaw support rods extend into the tubular member.

The one or more jaw support rods may function to assist a user in aligning a feature of interest between two or more opposing jaws, assist in creating a gripping force between the two opposing jaws, provide support to one or more jaws, extend through one or more tubular members and/or tubular members, or any combination thereof. The one or more jaw support rods may be a leg, a jaw shaft, or both. The one or more jaw support rods may extend through a central portion of the tubular member and the one or more jaw support rods are movable relative (i.e., parallel, axially, or both) to the tubes. The jaw support rods may be generally any shape that will perform the recited functions. The jaw support rods may be any light weight material that is strong enough to support the two opposing jaws and to support the gripping action of the jaws. The one or more jaw support rods may have a cross-section that is a solid cylindrical rod, a hollow cylindrical rod, a half circle shape, or a combination thereof. The jaw support rods may include one or more flat portions, may include non-arcuate portions, may be asymmetrical, or a combination thereof. The jaw support rods may be flexible, rigid, conductive, elastically deformable, or a combination thereof. Preferably, the one or more jaw support rods may form the jaw and fold back upon itself to form an opposing leg of the jaw. For example, the jaw support rods may extend out of the tube and curve back into the tubular member so that the portion extending out of the tubular member forms the jaws. The one or more jaw support rods may extend through and out the tubular member at the distal end of the tubular member, at the proximal end of the tubular member, or a both. The one or more jaw support rods may extend out of the distal end of the tubular member and may have a functional attachment connected to the distal end of the one or more jaw support rods. The functional attachment may be connected to one or both of two opposing jaws or an attachment with the functional equivalent of performing a gripping function. The one or more jaw support rods may be adjacent to, extend along opposing sides, surround, or a combination thereof the cutting assembly inside the tubular member. The one or more jaw support rods may terminate in a distal end region of the tubular member, an inner tube, or both. The surgical device may be free of jaw support rods, blade support rods, or both. For example, when the surgical device is configured for open surgery the jaws may be exposed at all times and may be free of jaw support rods that assist in closing or opening the jaws. The one or more jaw support rods may include or be connected to one or more bias mechanisms.

The bias mechanisms may function to move the jaws, blade, or both from a release position to a retract position. The bias mechanism may work with a return mechanism. The bias mechanisms may function to create a closing force, a gripping force, or both. The bias mechanism may function to actuate the jaws closed without the need for any other devices or features, to retract the blade, or both. The bias mechanism may function to bias the jaws closed, bias the jaws open, or both. The bias mechanism may only close the jaws. The bias mechanism may only open the jaws. The bias mechanism may be a combination of one or more tubes (e.g., a tubular member or an outer tube), one or more arcuate sections, or preferably a combination of both. The bias mechanism may cause the jaws to rotate about an axis. A bias mechanism may be in communication with each jaw individually. The bias mechanism may be a jaw closure mechanism. The jaw bias mechanism may be connected to a first link, a second link, a third, link, a fourth link, or a combination thereof. The bias mechanism may be the device that closes the jaws and the return mechanism may return the jaws to a resting state when a bias force is removed. The bias mechanism may bias both the arms and a valve simultaneously so that the jaws and valve are moved from an open position to a closed position. The bias mechanism may only bias the jaws from an open position to a closed position and the biasing of the jaws by the bias mechanism may simultaneously bias the valve from an open position to a closed position.

The one or more jaws, one or more valves, or both function to move between an open position and a closed position. The open position is a position where tissue may extend between the jaws. The open position is a position where fluid may extend through the valve, the fluid lines, the fluid openings, or a combination thereof. A gap may exist between the jaws when the jaws are in the closed position. For example, the gap may create a space between the jaws so that the feature of interest is not damaged by the jaws when the jaws are closed. The gap may be sufficiently large to not damage the feature of interest. The gap may be about 0.01 mm or more, about 0.05 mm or more, about 0.1 mm or more, about 0.5 mm or more, or about 1 mm or more. The gap may be about 5 cm or less, about 3 cm or less, about 1 cm or less, about 7 mm or less, about 5 mm or less, or about 3 mm or less. The open position may be a default position. The jaws, valves, or both may change from an open position to a closed position or vice versa. The closed position may be where the jaws grip a feature of interest. The closed position may be where the valve prevents fluid from moving through the valve, the fluid line, the fluid openings, or a combination thereof. The closed position may be a default position and the jaws, valve, or both may be biased to the closed position. As the valve is moved from the open position to the closed position the amount of fluid flow may be gradually decreased through the fluid openings.

The one or more fluid openings may function to allow fluid to pass into the jaws, out of the jaws, through the jaws, or a combination thereof. The one or more fluid openings may be located on a portion of a jaw that faces another jaw (e.g., a face of the jaw). The one or more fluid openings may be a hole within the conduction plate, face, teeth, contact surface, or a combination thereof. The one or more fluid openings may permit fluids to extend into or out of the jaws. Preferably, the one or more fluid openings permit a gas to extend into or out of the jaws. More preferably, the fluid openings allow for vacuum to move air into the jaws. The fluid openings may allow vacuum (e.g., negative pressure) to assist in holding a feature of interest in contact with a face, conduction plate, jaw, contact surface, or a combination thereof, while a gripping force is created. The fluid openings may have any shape so that fluid may be pulled thorough the fluid openings to assist in holding a feature of interest in place. The fluid openings may be square, round, oval, rectangular, diamond, "U" shaped, half "U" shaped, linear, arcuate, two or more parallel openings, or a combination thereof. The fluid openings may have a constant cross-sectional thickness from an entrance to an exit of the fluid openings. The fluid openings may have a cross-sectional thickness that decreases as the fluid openings extend from the entrance to the exit of the fluid openings (e.g., may be cone shaped if the fluid openings are circular). The fluid openings may be located in a face, conduction plate, mesh, teeth, between teeth, in a channel, or a combination thereof. The one or more fluid openings may allow fluid to be pulled into the fluid openings without a feature of interest being pulled into the fluid openings. The fluid openings may extend through a face of each of the jaws.

The face may function to be a contact surface of each of the jaws. The face may contact the feature of interest and assist in holding the feature of interest in place. The face may be smooth, include tooth, include mesh, include a conduction plate, include one or more of the fluid openings, or a combination thereof. Preferably, the face contacts a feature of interest and assists in retaining the feature therein so that a feature of interest is retained between the jaws. The face may be made of metal, plastic, a conductive material, an insulating material, a smooth material, a rough material, a material that will not damage an anatomical feature, steel, iron, nickel, stainless steel, copper, silver, silver coated, steel coated, or a combination thereof. Preferably, at least a portion of the face may be a conduction plate that assists in conducting power from the surgical device to a feature of interest.

The conduction plate functions to transfer power, heat, cool, or a combination thereof from the jaws of the surgical device to a feature of interest (e.g., tissue, veins). The conduction plates may both conduct power to a feature of interest and assist in gripping a feature of interest. The conduction plate may be attached to the jaws and may conduct power through the jaws. The conduction plate may be connected to a portion of the jaws that has insulative properties (e.g., a protective cover). The conduction plate may be in communication with one or more wires so that the conduction plate may provide power, heat, or both to a feature of interest. The conduction plate may be made of metal and may be connected to a plastic piece, ceramic piece, or both. The conduction plate may be made of steel, iron, a surgical steel, or a combination thereof. The conduction plate may include a non-stick coating (e.g., Teflon®). The conduction plate may extend around an outer perimeter, an inner perimeter, or both of the jaws. The conduction plate may be a solid plate that is one piece. The conduction plate may be a plurality of conductive pieces that are individually connected to the jaws. The conduction plate may be a mesh. The conduction plate or mesh may be one or more wires. The conduction plate or mesh may be a plurality of interwoven wires. The conduction plate or mesh may be wires that are crisscrossed together to provide gripping portions with fluid openings between the gripping portions. The mesh may create a gripping surface similar to teeth. The mesh may be provided instead of teeth.

The teeth may function to assist in holding a feature of interest between two jaws. The teeth may function to prevent the feature of interest from being removed from between two jaws. The teeth may be "V" shaped, rectangular, square, oval, or a combination thereof. The teeth may be free of sharp edges (e.g., two or more sides that converge to create a point or line). The teeth may include sharp edges. The teeth may create a peak so that a portion of a feature of interest may extend between the peaks into the valleys so that the feature of interest is retained between the jaws, so that the feature of interest is prevented from being removed from the jaws, or both. The teeth may be an extension of the conduction plate. The teeth may be located in an alternating fashion with the fluid openings. The teeth may include one or more fluid openings. The teeth may assist in holding the feature of interest in place as the jaws move from an open position to a closed position. The teeth may work in conjunction with the fluid openings so that the feature of interest is retained between the jaws. The teeth, fluid openings, or both may assist in preventing a feature of interest from being removed from the jaws when a cutting assembly is being used to cut the feature of interest.

The cutting assembly may be any assembly of parts capable of cutting. The cutting assembly may function to cut tissue, veins, arteries, an anatomical feature, a feature of interest, or a combination thereof during a surgical procedure. The cutting assembly may be any cutting assembly that may be used in surgery, for example laparoscopic surgery or open surgery. The cutting assembly may be an assembly of parts that may fit inside the tubular member and/or tube, extend through the stylet and/or tubular member, extend between the pair of opposing jaws, extend between legs, extend between legs and jaws, extend between jaw support rods, extend between jaws, extend into a channel, or a combination thereof. The cutting assembly may be any assembly of parts capable of rotating independent of the tubular member or in combination with the tubular member. The cutting assembly may be actuated to perform a cutting function by an operable mechanism. The cutting assembly may be any cutting assembly that may generally be comprised of a blade, a blade shaft, or a combination thereof.

The blade may function to cut a feature of interest. The blade may be any cutting tool that may be used in surgery, for example laparoscopic surgery or open surgery. The blade may be any cutting device that may be extended and retracted through the tubular member. The blade may extend along a stylet. The blade may be made of any material that may be sharpened; is strong enough to cut a feature of interest; is biocompatible; that may conduct electricity; or a combination thereof. The blade may be any shape so that the blade may fit inside the tubular member and extend into the channel formed between the two opposing jaws, between two legs connected to a jaw, or both so that a feature of interest may be cut. The blade may be substantially solid along its length. The blade may have a length so that the blade is sufficiently long to cut a feature of interest. The maximum length of the blade may be equal to the length of the jaws. The length of the blade may be substantially equal to that of the protrusions of the camming shaft. The length of the blade may be less than that of the protrusions. The blade may include one or more recesses. The blade may be sufficiently small so that the blade may be housed in the tubular member, tube, or both of a stylet during movement, insertion, or both. The blade may be extended into, and retracted from, the channel in the two opposing jaws. The distal end of the blade may have a shaped edge. The blade may extend distal of the jaws. The blade may conduct power. The blade may conduct a therapy current. The blade may conduct bipolar energy, monopolar energy, or both. The proximal end of the blade may be attached to a blade support rod.

The blade support rod may function to support the blade and assist in moving the blade axially. The blade support rod may extend the blade axially along the axis of the tubular member, the stylet, or both and out of the tubular member, stylet, or both (e.g., into the channel formed by the two opposing jaws). The blade support rod may move the blade axially upon movement of the operable mechanism, the operable mechanism, the first link, or a combination thereof. The blade support rod may function to extend and/or retract the blade via an operable mechanism. The blade support rod may be used to actuate a blade during surgery. The blade support rod may be of shape and size to actuate a blade inside a tubular member. For example the blade support rod may be a wire, shaped metal, a rod, a plurality of combined longitudinal pieces, or any similar rigid structure that may fit in and extend through the tubular member. The blade support rod may be connected to a trigger, a slider, or both. The blade support rod may be made of a material that is lightweight, but strong enough to extend a blade through a feature of interest thereby cutting the feature of interest. The blade support rod has a distal end and a proximal end. A blade may be attached to a distal end, a distal end region, or both of the blade support rod. The blade support rod may extend through, around, along, next to, parallel to, or a combination thereof a pivot that connects the first jaw, and the second jaw together.

The one or more pivots may function to connect a first jaw and a second jaw together. The one or more pivots may function to create a point that the first jaw and the second jaw move about between an open position and a closed position. The one or more pivots may be a pin. The one or more pivots may be a movable connection location between two or more jaws. Each jaw may include one or more holes or recesses that receive a connection device (e.g., a pin) that movably connects the jaws together. The one or more pivots may function to assist in opening and closing the valves. Each jaw may include a pivot that allows the jaws to rotate towards each other and allow each of the jaws to move between an open position and a closed position. The pivots may close jaws, open jaws, close valves, open valves, or a combination thereof. The one or more pivots may assist in activating and deactivating an atraumatic tissue control.

The atraumatic tissue control (ATC) may function to assist in holding a feature of interest on one jaw, between the jaws, or both while the jaws are moved to a closed position or a partially closed position. The ATC may function to prevent the feature of interest from slipping out from between the jaws. The ATC may prevent tissue damage while the jaws are closed. The ATC may allow for jaws with a smooth surface, without teeth, or both to grip a feature of interest. The ATC may hold the feature of interest in place by creating a negative pressure (e.g., suction or vacuum) on the feature of interest so that the feature of interest is free of movement on the jaws while the jaws close. The ATC may remove the negative pressure or decrease the amount of negative pressure as the jaws move into contact with the features of interest. The ATC may include one or more valves, one or more legs, one or more orifices, one or more fluid lines, one or more suction sources, one or more vacuum sources, one or more fluid passageways, or a combination thereof.

The one or more fluid passageways may function to permit fluid to extend between one or both of the jaws and a region outside of the surgical device (e.g., ambient around the surgical device of a suction source). The one or more fluid passageways may be free of connection with a hospital suction source or a surgical ward suction source. The fluid passageways may be connected to ambient (i.e., the room air that is not subject to any conditioning). The fluid passageway may be connected to a suction source of the surgical device. The one or more fluid passageways may extend along or through a first jaw, a second jaw, or both. The one or more fluid passageways may extend through or along a stylet. The one or more fluid passageways may extend along or through a jaw support rod, a tube, or both. The one or more fluid passageways may be located internal to one or more parts of the surgical device. All or a portion of the fluid passageways may extend external to one or more parts of the surgical device. The fluid passageways may be an absence of material that a fluid may flow through. The fluid passageways may be an opening within the housing that the valves, fluid lines, fluid openings, or a combination thereof extend through, are connected to, are located within, or a combination thereof. The fluid passageways may protect the fluid lines, the valves, or both. The fluid passageways may guide fluid from the fluid passageway to a region outside of the surgical device without fluid lines. The fluid passageways may house one or more fluid lines, one or more valves, or both.

The one or more valves may function to restrict or prevent fluid flow through the fluid passageways, the fluid line, or both. The one or more valves may prevent fluid from passing through the one or more fluid openings. The one or more valves may restrict movement of fluid into the fluid openings that are contained in the jaws. The one or more valves may be any type of valve that may be opened and closed by movement of one or more jaws, one or more pivots, or both. A portion of the jaws may be part of the valves. The valves may restrict fluid flow through the fluid passageways, the fluid lines, or both. The opening size of the valve may be directly proportional to the opening size of the jaws. Thus, if the jaws are 100 percent open the valve may be 100 percent opening. The opening of the valve and the opening of the jaws may be directly proportional but the valve may close before the jaws close or the jaws may close before the valve close. The closing of the valve and the jaws may be within about ±20 percent or less. For example, the valve may close when the jaws are about 80 percent closed. The valve may pinch the fluid line. The valve may fold the fluid line. The valve may compress the fluid line. The valve may be placed within the fluid line. The valve may be a ball valve, a gate valve, a globe valve, diaphragm valve, butterfly valve, check valve, plug valve, needle valve, or a combination thereof. Preferably, the valve is a barrel valve, a pinch valve, or both.

The barrel valve may function to occlude the fluid passageway, the fluid line, or both to prevent the movement of fluid between the fluid openings and a region outside of the surgical device. The barrel valve may include one or more orifices, one or more legs, or both that the fluid passageway, the fluid lines, or both extend through. The fluid line, the fluid passageway, or both may extend through one or more orifices and upon movement of the jaws, the fluid line, the fluid passageway, or both may be closed by the barrel valve. The orifice may remain static while the jaws move between an open position and a closed position. The orifice may rotate as the jaws rotate so that the orifice assists in closing the valve. The orifice may align with a jaw and as the jaw rotates between an open position and a closed position the orifice may rotate to open and close the fluid passageway, the fluid line, or both. The orifice may remain static and the barrel may move relative to the orifice to close the fluid passageway, the fluid line, or both. A proximal end of the orifice may be closed by a pinch leg. The pinch leg may cover a proximal end of the orifice. The pinch leg may contact a fluid line and bend the fluid line or fluid passageway so that fluid is restricted through the fluid passageway, the fluid line, or both. The pinch leg may extend into the orifice and compress or block the fluid line, the fluid passageway, or both. The orifice may be a first opening and a second opening and the pinch leg may extend between the first opening and the second opening. The pinch leg may cause the fluid line, fluid passageway, or both to move from being linear to being "U" shaped. The pinch leg may move the fluid line, fluid passageway, or both from being linear to being "L" shaped. The pinch leg may completely compress the fluid passageway, the fluid line, or both. The pinch leg may be movable relative to the orifice or into the orifice. The pinch leg may be part of one or more pinch valves.

The pinch valve may function to close the fluid passageway, the fluid line, or both when the jaws move about a pivot. The pinch valve may include a pinch leg, a contact leg, or both. The pinch valve may create a nip, a pinch point, a squeeze location, a compression location, or a combination thereof. The pinch valve may have a contact side and a pinch side. The contact side may have a contact leg. The contact leg may have a portion that that receives or holds a fluid passageway, a fluid line, or both. The contact leg may support the fluid line so that when a pinch leg rotates into contact with the fluid line, the fluid line is compressed, restricted, closed, or a combination thereof. The contact leg may be flat, have a groove, have a "U" shaped portion, or a combination thereof. The contact leg may prevent lateral movement of the fluid line so that the fluid line remains aligned with the pinch leg as the pinch leg rotates towards the contact leg.

The pinch leg functions to compress or close a fluid passageway, a fluid line, or both. The pinch leg may have a contact location. The contact location of the pinch leg may be wider than a remainder of the pinch leg. The contact location may contact the fluid line, the fluid passageway, or both to restrict or prevent movement of fluid throughout the fluid line, the fluid passageway, or both. The pinch leg may rotate toward the contact leg to pinch and close the fluid line.

The fluid line may function to carry a fluid between the fluid openings and a region outside of the surgical device. Preferably, the fluid line carries air from the fluid openings to outside of the surgical device so that a negative pressure is formed at the jaws. The one or more fluid lines may be an integral part of the jaws. The one or more fluid lines may be made of a bio compatible material. The one or more fluid lines may be made of or include plastic, metal, a elastic material, rubber, nylon, nitrile, silicone, poly-vinyl chloride (PVC), polyurethane (PU), or a combination thereof. The one or more fluid lines may be fully open, fully closed, or any position therebetween. The one or more fluid lines may be connected to a vacuum source, suction, ambient, or a combination thereof.

The vacuum source, suction, ambient, or a combination thereof may be a suction source as discussed herein. The suction source may be part of the surgical device. The suction source may function to move fluid from the jaws.

The suction source may be a pressure difference between inside of a patient and outside of a patient. The suction source may be a negative pressure. The suction source may be a different between a high pressure in a patient or surgical site and an atmospheric pressure (i.e., ambient). The suction source may create a vacuum that assists in holding a feature of interest on the jaws. The suction source may be created by a pump and preferably a vacuum pump. The vacuum pump may create a negative pressure that moves a gas from a positive pressure area or an atmospheric pressure area so that a feature of interest may be held against the jaws. The suction source may created by forming a release where positive pressure may be expelled from a surgical site. For example, if gas is pumped into a surgical site the surgical site may be positive pressure, and the fluid openings and fluid passageway may allow fluid to escape from the surgical site, creating negative pressure. The fluid may extend from inside of a surgical site to atmospheric pressure creating suction at a face of one or more jaws of forceps. For example, one device may pump an inert gas into a surgical site so that a cavity within the surgical site is expanded, and the gas may be expelled through a passageway, and the movement of the gas out of the passageway may create suction at a face of one or both of the jaws that retains a feature of interest in contact with the jaws.

FIG. 1 is a surgical device 4 having a proximal end 90 and a distal end 92. The proximal end 90 includes a handpiece 50 including a clamp trigger 52 that actuates the jaws 10 and a cut trigger 54 that actuates a blade (not shown). The handpiece 50 includes a housing 56 that is connected to a stylet 8. The stylet 8 includes a tube 9 with jaws 10 at the end, and the jaws 10 are connected to jaw rods (not shown) and a blade (not shown) that extend through the tube 9. The jaws 10 as shown are configured as forceps 6 that close to grip tissue.

Figure 1A:
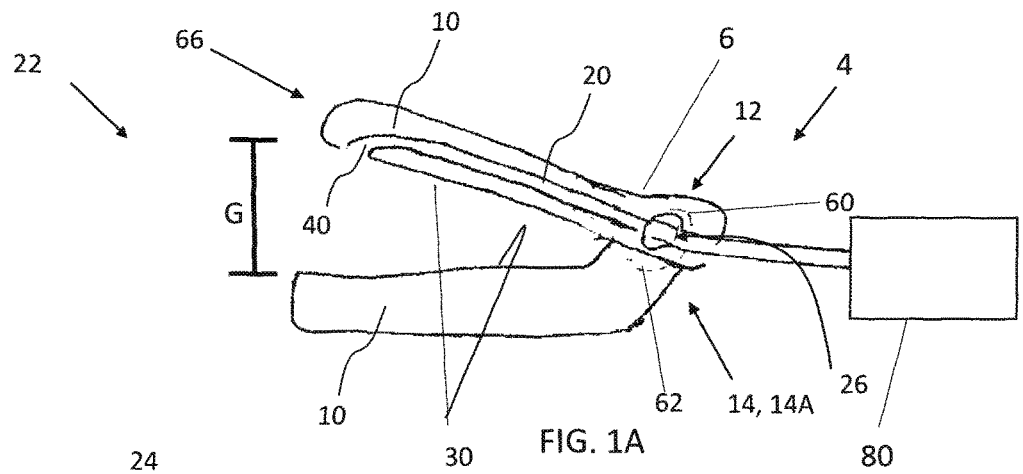
FIG. 1A is a side view of a surgical device having a barrel valve for closing a fluid line with the barrel valve being in an open position.
Figure 1B:
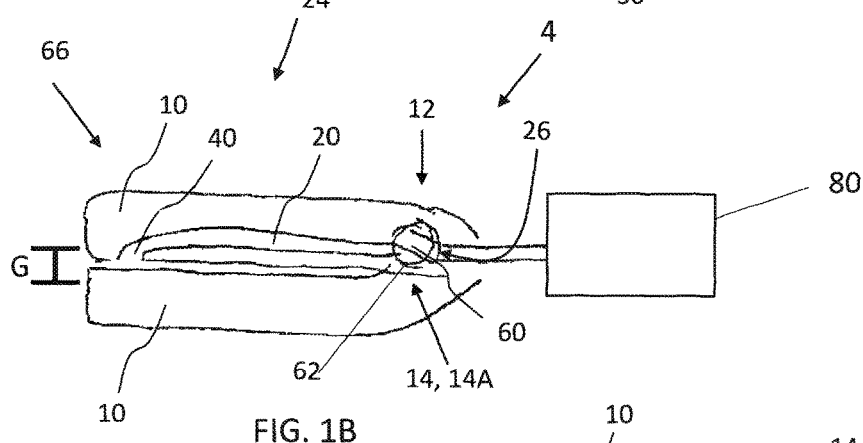
FIG. 1B is a side view of the surgical device of FIG. 1A with the barrel valve being in a closed position.

FIGS. 1A and 1B illustrate a side view of a surgical device 4 configured as forceps 6 that include atraumatic tissue control 66. The surgical device 4 includes a plurality of jaws 10 movably engaged via a pivot 12. Each of the jaws 10 include a face 30 that are movable towards and away from each other. The atraumatic tissue control 66 includes a fluid passageway 26 that includes a fluid line 20 having a fluid opening 40 that is routed through a first jaw 10 and a valve 14 so that the fluid line 20 may be opened and closed. The fluid passageway 26 is connected to a vacuum source 80. The suction source removes fluid through the fluid passageway 26 and creates negative pressure relative to ambient surroundings around the patient. The valve 14 being a barrel valve 14A located at the pivot 12 that can be opened and closed. As shown in FIG. 1A, the barrel valve 14A is in an open position 22 so that fluid in the fluid line 20 may pass through the fluid line 20 and the barrel valve 14A unobstructed. Fluid can be pulled through the fluid opening 40 in the jaw 10 so that tissue (not shown) can be held in contact with the jaw 10. The barrel valve 14A includes an orifice 60 that receives the fluid line 20 and a pinch leg 62 that is free of contact with the fluid line 20 when the surgical device 4 is in the open position 22. As shown in FIG. 1B, a gap (G) between the jaws 10 is decreased by pivoting the jaws 10 relative to one another so that the barrel valve 14A compresses the fluid line 20, resulting in the fluid line 20 and surgical device 2 being in a closed position 24, and preventing fluid in the fluid line 20 from passing through the barrel valve 14A. When the jaws 10 close, the pinch leg 62 rotates and contacts the fluid line 20 so that the fluid line 20 is closed between the orifice 60 and the pinch leg 62.

Figure 2A:
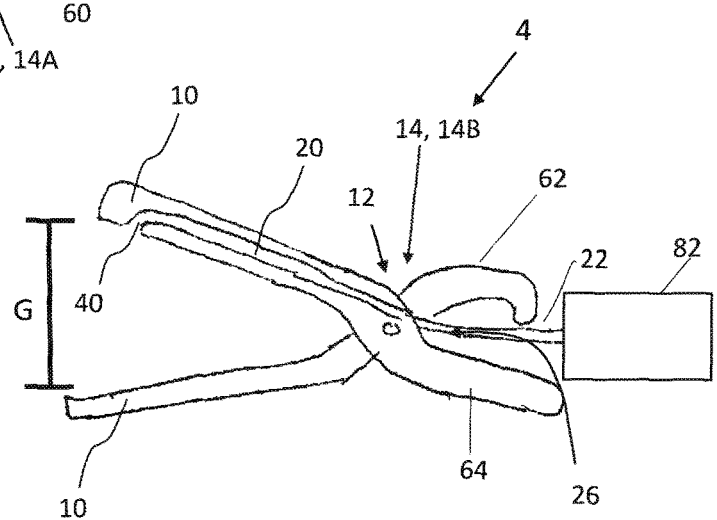
FIG. 2A is a side view of a surgical device having a pinch valve for closing a fluid line with the pinch valve being in an open position.
Figure 2B:
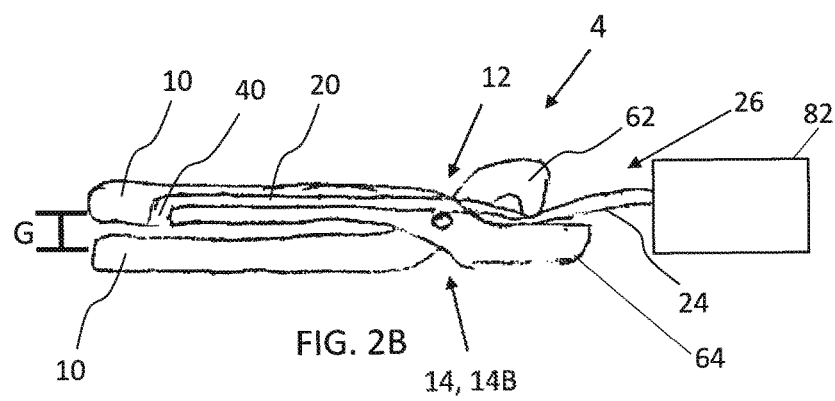
FIG. 2B is a side view of the surgical device of FIG. 2A with the pinch valve in a closed position, closing the fluid line.

FIGS. 2A and 2B illustrate a side view of a surgical device 4 connected to ambient 82. The ambient 82 has a lower pressure than a pressure inside of a patient so that the positive pressure within the patient escapes through the passageway 26 to the ambient 82 creating negative pressure. The surgical device 4 includes a plurality of jaws 10 movably engaged via a pivot 12. A fluid passageway 26 includes a fluid line 20 having a fluid opening 40 is routed through a first jaw 10 and valve 14 so that the fluid line 20 may be opened and closed via the valve 14 which is a pinch valve 14B. As shown in FIG. 2A, the fluid line 20 and surgical device 4 are in an open position 22 so that fluid in the fluid line 20 may pass through the pinch valve 14B unobstructed. As shown, the pinch leg 62 and contact leg 64 are spaced apart and the fluid line extends therebetween. In FIG. 2B, a gap (G) between the jaws 10 is decreased by pivoting the jaws 10 relative to one another so that the pinch leg 62 and the contact leg 64 of the pinch valve 14B pinches the fluid line 20, resulting in the fluid line 20 and surgical device 2 being in a closed position 24, and preventing fluid in the fluid line 20 from passing through the pinch valve 14B.

Figure 3:
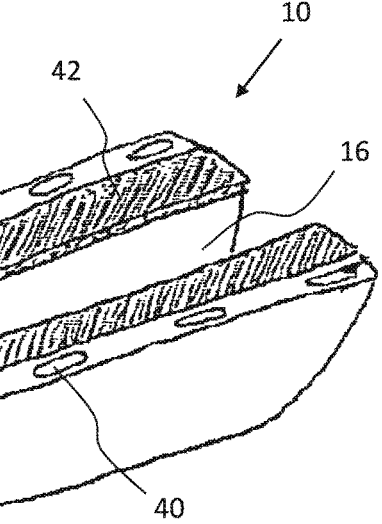
FIG. 3 is a perspective view of a jaw of a surgical device having a conduction plate and a plurality of fluid openings.
Figure 4:
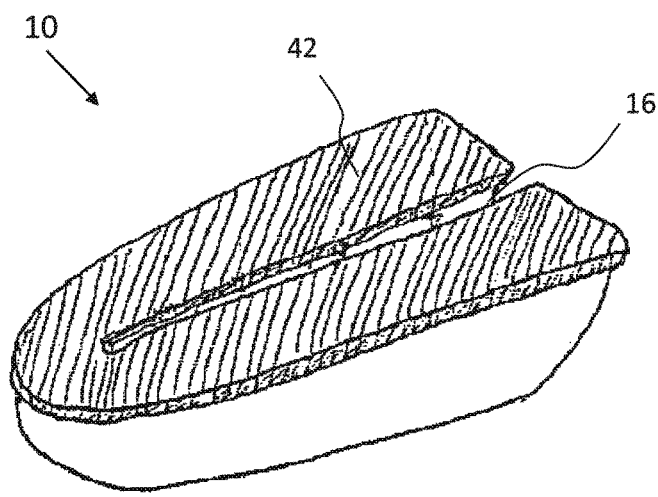
FIG. 4 is a perspective view of a jaw of a surgical device having a conduction plate and a central channel.
Figure 5:
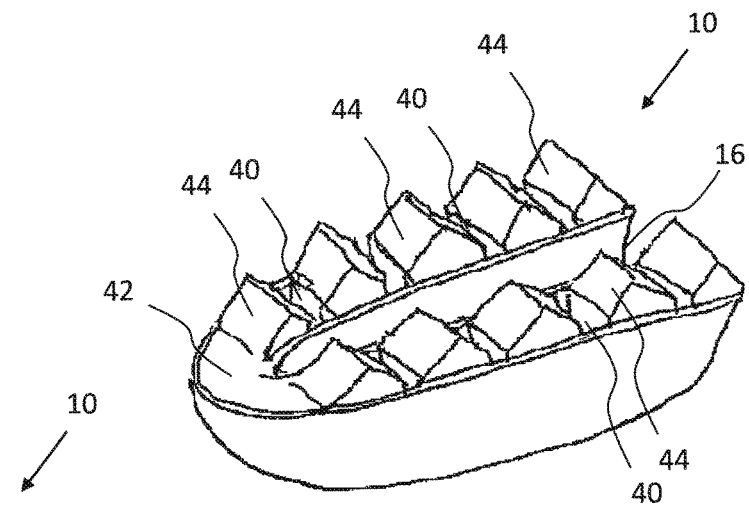
FIG. 5 is a perspective view of a jaw of a surgical device having a conduction plate with a plurality of teeth and fluid openings.
Figure 6:
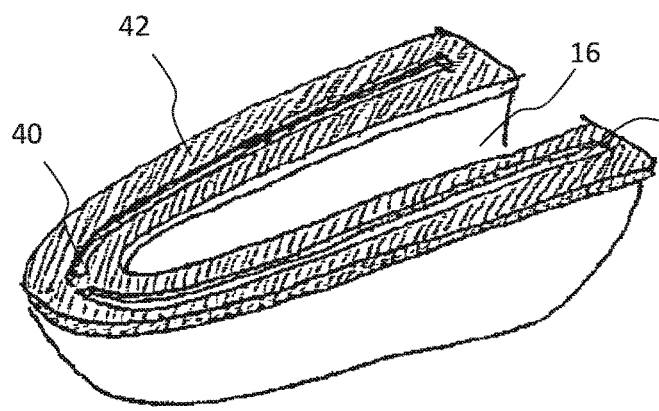
FIG. 6 is a perspective view of a jaw of a surgical device having a conduction plate with a plurality of fluid opening.

FIGS. 3-6 illustrate perspective views of various jaws 10 for a surgical device. As shown in FIG. 3, the jaw 10 includes a plurality of fluid openings 40 abutting a conduction plate 42 extending around a channel 16. FIG. 4 illustrates a jaw 10 having a central channel 16 surrounded by a conduction plate 42 and the conduction plate being free of fluid openings. The central channel 16 includes fluid openings (not shown) that allow fluid to be moved through the central channel 16. FIG. 5 shows the jaw 10 with a conduction plate 42 comprising a plurality of teeth 44 spaced apart by a plurality of fluid openings 40, the conduction plate 42 surrounding a central channel 16. The teeth 44 and the fluid openings 40 are alternate around the jaw 10. As shown in FIG. 6, the conduction plate 42 of the jaw 10 is free of teeth and includes a plurality of slotted fluid openings 40 surrounding the central channel 16.

Figure 7:
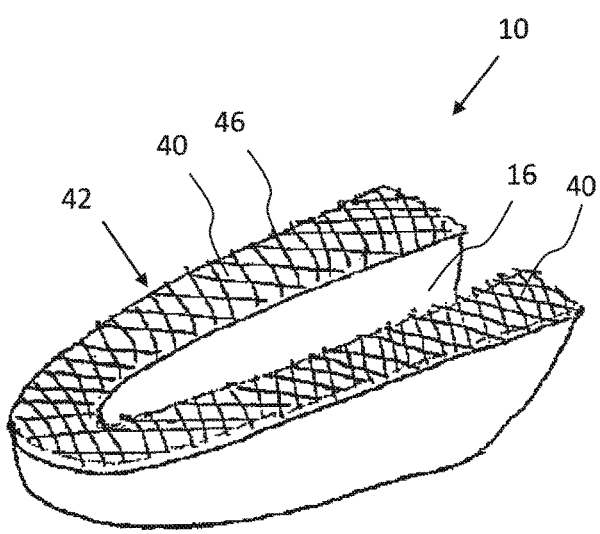
FIG. 7 is a perspective view of a jaw of a surgical device having a mesh conduction plate.

FIG. 7 illustrates a perspective view of a jaw 10 of a surgical device. The jaw 10 includes a conduction plate 42 having a mesh layer 46 with a plurality of fluid openings 40 surrounding a channel 16 of the jaw 10.

Figure 8:
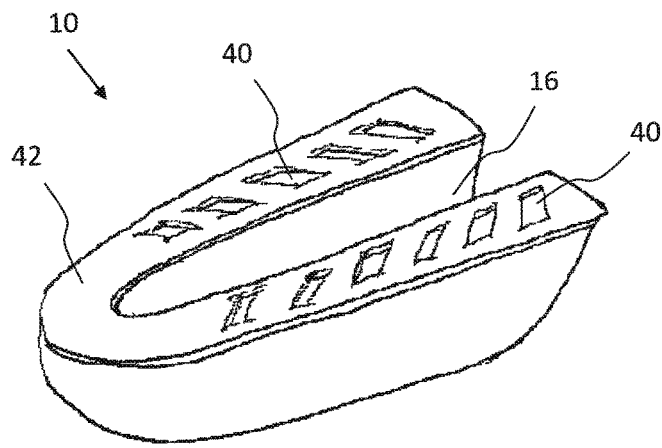
FIG. 8 is a perspective view of a jaw of a surgical device having a conduction plate with a plurality of slotted fluid openings.
Figure 9:
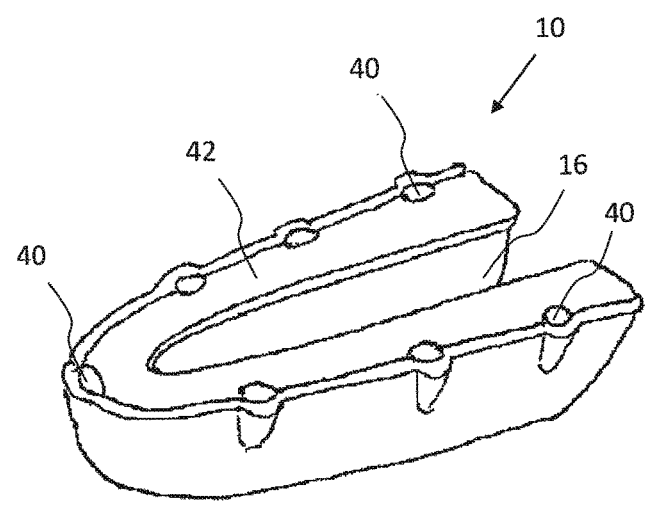
FIG. 9 is a perspective view of a jaw of a surgical device having a conduction plate with a plurality of peripheral fluid openings.
Figure 10:
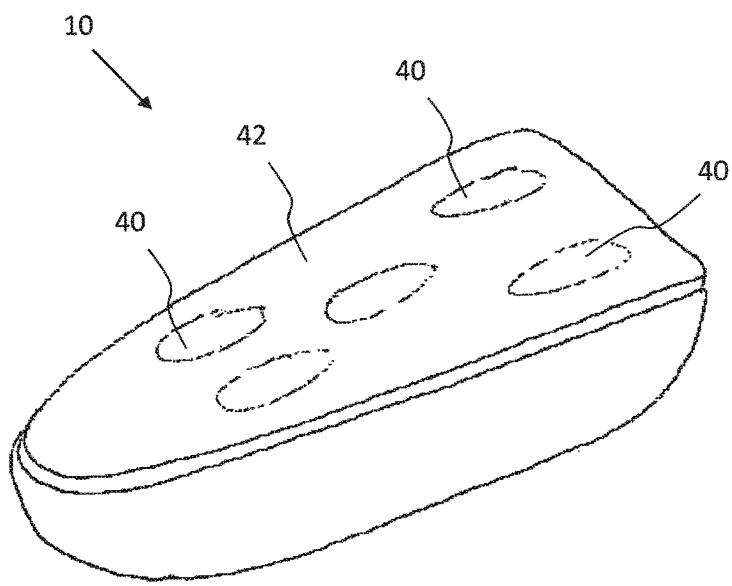
FIG. 10 is a perspective view of a jaw of a surgical device having a conduction plate with a plurality of fluid openings.

FIGS. 8-10 each illustrate a perspective view of a jaw 10 for a surgical device, each jaw 10 having a conduction plate 42 with a plurality of fluid opening 40 positioned in different locations. As shown in FIG. 8, the fluid openings 40 are slotted throughout the conduction plate 42 and surround a channel 16. As shown in FIG. 9, the fluid openings 40 are located along an outer peripheral edge of the conduction plate 42, while the inner edge of the conduction plate 42 surrounds a channel 16. Alternatively, as shown in FIG. 10, a conduction plate 42 has a plurality of fluid openings 40 disposed throughout the conduction plate with the jaw 10 being free of a channel.

Figure 11:
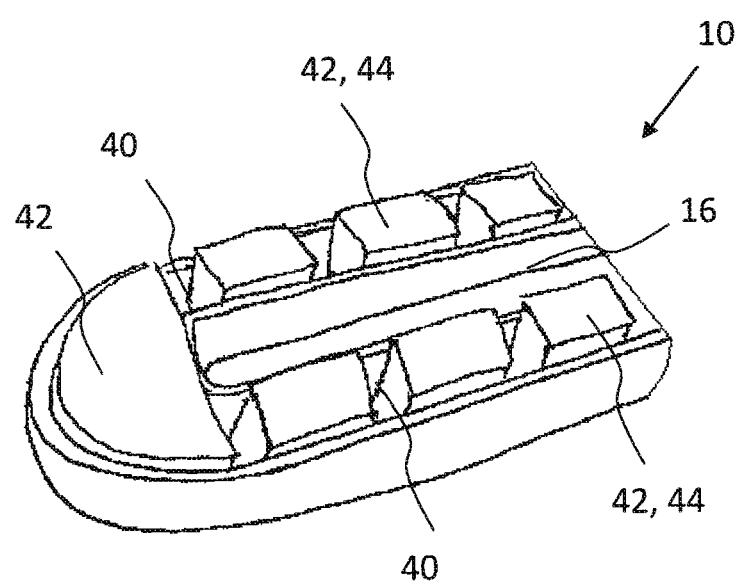
FIG. 11 is a perspective view of a jaw of a surgical device having a plurality of conduction plates and fluid openings.

FIG. 11 illustrates a perspective view of a jaw 10 for a surgical device. The jaw 10 includes a plurality of conduction plates 42 surrounding a central channel 16. A portion of the conduction plates 42 includes teeth 44 that are spaced apart by a plurality of fluid openings 40.

Any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

The disclosures of all articles and references, including patent applications and publications, are incorporated by reference for all purposes. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of the elements, ingredients, components or steps. By use of the term "may" herein, it is intended that any described attributes that "may" be included are optional.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

It is understood that the above description is intended to be illustrative and not restrictive. Many embodiments as well as many applications besides the examples provided will be apparent to those of skill in the art upon reading the above description. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

4 Surgical Device
6 Forceps
8 Stylet
9 Tube
10 Jaw
12 Pivot
14 Valve
14A Barrel Valve
14B Pinch Valve
16 Channel
20 Fluid Line
22 Open Position
24 Closed Position
26 Fluid Passageway
30 Face
40 Fluid Opening
42 Conduction Plate
44 Teeth
46 Mesh
G Gap
50 Hand Piece
52 Clamp Trigger
54 Cut Trigger
56 Housing
60 Orifice
62 Pinch Leg
64 Contact Leg
66 Atraumatic Tissue Control
80 Vacuum Source
90 Proximal End
92 Distal End

We claim:

1. A surgical device comprising:
a first jaw having a face;
a second jaw having a face that is substantially adjacent the face of the first jaw when the first jaw and the second jaw are in a closed position;
a pivot connecting the first jaw and the second jaw together so that the first jaw and second jaw are movable between an open position and the closed position;
one or more fluid passageways extending along the first jaw, the second jaw, or both and to a region outside of the surgical device so that fluid passes through the first jaw, the second jaw, or both; and
a valve connected to, and actuated by a trigger together with, the first jaw, the second jaw, or both, the one or more fluid passageways extending through the valve so that when the first jaw and the second jaw are in the open position the valve is open and fluid can extend through the one or more fluid passageways and when the first jaw and the second jaw are in the closed position the valve is closed and fluid is prevented from flowing through the one or more fluid passageways.

2. The surgical device of claim 1, wherein the valve is a barrel valve or a pinch valve.

3. The surgical device of claim 2, wherein the one or more fluid passageways are one or more fluid lines and the barrel valve includes an orifice that receives the one or more fluid lines and a pinch leg that rotates into contact with the one or more fluid lines that extend into the orifice.

4. The surgical device of claim 2, wherein the pinch valve includes a pinch leg and a contact leg, and the one or more fluid passageways are one or more fluid lines and the one or more fluid lines extend between the pinch leg and the contact leg.

5. The surgical device of claim 4, wherein the pinch leg and the contact leg contact the one or more fluid lines when the first jaw and the second jaw are in a closed position so that one or more fluid lines are closed by the pinch leg and the contact leg.

6. The surgical device of claim 1, wherein the one or more fluid passageways are connected to a suction source located in the region outside of the surgical device and the suction source moves fluid from the face of the first jaw, the second jaw, or both so that vacuum is created.

7. The surgical device of claim 6, wherein the suction source is a vacuum pump.

8. The surgical device of claim 1, wherein the one or more fluid passageways extend along a length of the first jaw, the second jaw, or both to a location proximate to the face of the first jaw, the face of the second jaw, or both.

9. A surgical forceps comprising:
a first jaw having a face;
a second jaw having a face that is substantially adjacent the face of the first jaw when the first jaw and the second jaw are in a closed position;
a pivot connecting the first jaw and the second jaw together so that the first jaw and second jaw are movable between an open position and the closed position to grip an anatomical feature between the first jaw and the second jaw when the surgical forceps are in the closed position; and
one or more fluid passageways extending between the face of the first jaw, the face of the second jaw, or both, wherein the one or more fluid passageways are actuated open by opening a valve thereby opening the fluid passageways in response to actuation of the first jaw, the second jaw, or both so that fluid passes through the face of the first jaw, the face of the second jaw, or both, in response to when the surgical forceps are actuated to be in the open position.

10. The surgical forceps of claim 9, wherein a positive pressure of a surgical site is expelled through the one or more fluid passageways so that suction is formed at the face of the first jaw, the face of the second jaw, or both.

11. The surgical forceps of claim 10, wherein the one or more fluid passageways are free of a connection with a vacuum source.

12. The surgical forceps of claim 9, wherein the surgical forceps include one or more valves that open the one or more fluid passageways when the first jaw and second jaw are open and close the one or more fluid passageways when the first jaw and the second jaw are closed.

13. The surgical forceps of claim 12, wherein the one or more fluid passageways are one or more fluid lines and the one or more valves are a barrel valve that includes an orifice for receiving the one or more fluid lines and a pinch leg so that closing of the first jaw and second jaw closes the one or more fluid lines between the orifice and the pinch leg.

14. The surgical forceps of claim 12, wherein the one or more fluid passageways are one or more fluid lines and the one or more valves are a pinch valve that includes a pinch leg and a contact leg so that closing of the first jaw and second jaw closes the one or more fluid lines between the contact leg and the pinch leg.

15. The surgical forceps of claim 9, wherein the face includes one or more conduction plates, one or more fluid openings, or both.

16. A surgical forceps comprising:
a first jaw having a face;
a second jaw having a face that is substantially adjacent the face of the first jaw when the first jaw and the second jaw are in a closed position;
a pivot connecting the first jaw and the second jaw together so that the first jaw and second jaw are movable between an open position and the closed position to grip an anatomical feature between the first jaw and the second jaw when the surgical forceps are in the closed position; and
one or more fluid passageways extending between the face of the first jaw, the face of the second jaw, or both and a region inside of the surgical device so that fluid passes through the face of the first jaw, the face of the second jaw, or both and the region inside of the surgical device; and
a barrel valve or pinch valve located at the pivot and actuated open to release the fluid when the first jaw and the second jaw of the surgical forceps are in the open position.

17. The surgical forceps of claim 16, comprising a return mechanism coupled to the first jaw, the second jaw, or both, and wherein the return mechanism assists in moving the first jaw, the second jaw, or both.

18. The surgical forceps of claim 16, comprising a protective covering coupled to the first jaw, the second jaw, or both.

19. The surgical device of claim 16, wherein the valve includes a pinch valve actuated open to release the fluid when the first jaw and the second jaw of the surgical forceps are in the open position, and comprising a pinch leg and the first jaw that are on opposite ends of the pivot, and comprising a contact leg and the second jaw that are on opposite ends of the pivot.

* * * * *

UNITED STATES PATENT AND TRADEMARK OFFICE
CERTIFICATE OF CORRECTION

PATENT NO. : 10,722,258 B2  
APPLICATION NO. : 15/850090  
DATED : July 28, 2020  
INVENTOR(S) : Batchelor et al.

Page 1 of 1

It is certified that error appears in the above-identified patent and that said Letters Patent is hereby corrected as shown below:

On the Title Page

Item (71), delete "GYRUS ACMI, INC.," and insert --GYRUS ACMI, INC., d/b/a Olympus Surgical Technologies America,-- therefor Item (73), delete "Gyrus Acmi, Inc.," and insert --Gyrus Acmi, Inc. DBA Olympus Surgical Technologies America,-- therefor Signed and Sealed this  
Thirteenth Day of October, 2020

Andrei Iancu  
*Director of the United States Patent and Trademark Office*